United States Patent
Dunfee (10) Patent No.: US 9,909,945 B2
(45) Date of Patent: Mar. 6, 2018

(54) METHODS AND APPARATUS FOR MEASURING ASPIRATION PRESSURE AT LOW ASPIRATION VOLUMES

(71) Applicant: William D. Dunfee, Newark, DE (US)

(72) Inventor: William D. Dunfee, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 309 days.

(21) Appl. No.: 14/432,983

(22) PCT Filed: Oct. 2, 2013

(86) PCT No.: PCT/US2013/062967
§ 371 (c)(1),
(2) Date: Apr. 1, 2015

(87) PCT Pub. No.: WO2014/055590
PCT Pub. Date: Apr. 10, 2014

(65) Prior Publication Data
US 2015/0276534 A1 Oct. 1, 2015

Related U.S. Application Data

(60) Provisional application No. 61/709,750, filed on Oct. 4, 2012.

(51) Int. Cl.
*G01N 35/10* (2006.01)
*G01L 19/00* (2006.01)
*B01L 3/02* (2006.01)

(52) U.S. Cl.
CPC .......... *G01L 19/00* (2013.01); *G01N 35/1016* (2013.01); *B01L 3/02* (2013.01); *B01L 2200/146* (2013.01); *G01N 2035/1034* (2013.01)

(58) Field of Classification Search
CPC ....... G01N 35/1016; G01N 2035/1018; G01N 2035/1025; G01N 35/10; G01N 35/1009;
(Continued)

(56) References Cited

U.S. PATENT DOCUMENTS 5,463,895 A 11/1995 Brentz
5,540,081 A 7/1996 Takeda et al.
(Continued)

FOREIGN PATENT DOCUMENTS

WO 98/53325 A1 11/1998
WO 2012/031222 A1 3/2012

OTHER PUBLICATIONS

PCT International Search Report and Written Opinion dated Dec. 20, 2013 (10 Pages).
(Continued)

*Primary Examiner* — Hezron E Williams
*Assistant Examiner* — Gedeon M Kidanu (57) ABSTRACT

A method adapted to allow aspiration verification of a liquid such as a biological liquid or liquid reagent at low aspiration volumes (e.g., less than 25 µL). The method includes attempting to aspirate a volume of a liquid into a probe at an aspiration frequency, measuring an aspiration pressure associated with the attempted aspiration of the liquid and providing a measured pressure signal, and filtering the measured pressure signal with a filter. The filter has a passband frequency containing the aspiration frequency and excluding the frequencies of a disturbance causing noise in the measured pressure signal. Apparatus for carrying out the method are provided, as are other aspects.

31 Claims, 7 Drawing Sheets

(58) Field of Classification Search
CPC ........... G01N 1/38; G01N 2035/00653; G01N 2035/00881; G01N 2035/0436; G01N 21/274; G01N 21/359; G01N 2201/129; G01N 2201/1293; G01N 2035/1034; G01N 35/0099; B01L 2200/146; B01L 2300/0654; B01L 2400/0478; B01L 3/0265; B01L 3/0268; B01L 3/0293; B01L 2300/0627; B01L 2300/12; B01L 2300/14; B01L 2400/0487; B01L 2400/06; B01L 2400/086; B01L 3/02; B01L 3/021; B01L 3/0217; A61M 1/3627; A61M 1/3639; A61M 1/3666; A61M 2205/3389; C12M 21/04; C12M 41/34; C12M 41/36; G01B 13/00; G01L 19/00; G01L 11/04; G01F 13/00
See application file for complete search history.

(56) References Cited

U.S. PATENT DOCUMENTS

| | | | |
|---|---|---|---|
| 6,022,747 A * | 2/2000 | Gherson | G01N 33/4905 436/148 |
| 6,158,269 A | 12/2000 | Dorenkott et al. | |
| 6,322,752 B1 | 11/2001 | Siddiqui et al. | |
| 6,370,942 B1 * | 4/2002 | Dunfee | G01M 3/26 73/1.74 |
| 7,477,997 B2 | 1/2009 | Kaplit | |
| 7,634,378 B2 | 12/2009 | Kaplit | |
| 7,792,647 B1 | 9/2010 | Ding et al. | |
| 7,804,599 B2 | 9/2010 | Calderoni | |
| 7,926,325 B2 | 4/2011 | Kaplit | |
| 8,026,101 B2 | 9/2011 | Bower et al. | |
| 8,287,820 B2 | 10/2012 | Williams et al. | |
| 2002/0177237 A1 * | 11/2002 | Shvets | G01N 1/2813 436/174 |
| 2005/0119600 A1 * | 6/2005 | Lucke | A61M 1/3627 604/6.15 |
| 2005/0282291 A1 * | 12/2005 | Pankratz | G01N 35/1016 436/180 |
| 2006/0017923 A1 * | 1/2006 | Ruchti | G01J 3/28 356/326 |
| 2006/0111872 A1 * | 5/2006 | Papadimitriou | G01N 27/9046 702/185 |
| 2009/0075386 A1 * | 3/2009 | Dunfee | G01N 35/1009 436/54 |
| 2010/0152601 A1 * | 6/2010 | Akiyama | A61B 5/08 600/538 |
| 2013/0143257 A1 * | 6/2013 | Small | G01N 35/1009 435/29 |

OTHER PUBLICATIONS

Extended EP Search Report dated May 4, 2016 of corresponding European Application No. 13843738.9, 4 Pages.

* cited by examiner

METHODS AND APPARATUS FOR MEASURING ASPIRATION PRESSURE AT LOW ASPIRATION VOLUMES

RELATED APPLICATIONS

The present application claims priority from U.S. Provisional Patent Application Ser. No. 61/709,750, filed Oct. 4, 2012, entitled "METHODS AND APPARATUS FOR MEASURING ASPIRATION PRESSURE AT LOW ASPIRATION VOLUMES" which is hereby incorporated herein by reference in its entirety for all purposes.

FIELD

The present invention relates generally to methods and apparatus for determining aspiration quality during aspiration of liquids in clinical analyzers.

BACKGROUND

In testing within clinical laboratories to measure various chemical constituents of body fluids obtained from patients, such as whole blood, blood serum, blood plasma, and the like, fully-automated clinical analyzers may reduce the number of trained technicians required to perform the analyses, improve accuracy of the testing, and reduce the cost per test.

Typically, an automated analyzer includes an automated aspirating and dispensing apparatus, which is adapted to aspirate a liquid (e.g., a sample of biological liquid or a liquid reagent) from a container and dispense the liquid into a reaction vessel (e.g., a cuvette). The aspirating and dispensing apparatus typically includes a pipette (otherwise referred to herein as a "probe") mounted on a moveable arm or other automated mechanism, to perform the aspiration and dispensing functions and transfer the sample to the reaction vessel.

During the aspiration operation, the moveable arm, which may be under the control of a robotic controller, may position the probe above the container, and descend the probe into the container until the probe is partially immersed in the liquid (e.g., biological liquid sample or liquid reagent) in the container. A pump or other aspirating device is then activated to draw in (aspirate) a portion of the liquid from the container into the interior of the probe. The probe is then ascended (retracted) from the container such that the liquid may be transferred to the reaction vessel for testing. During or after the aspiration, an aspiration pressure signal may be analyzed to determine any anomalies, i.e., check for the presence of a clog or the presence of air should there be insufficient liquid remaining to carry out the desired aspiration.

Conventional systems are able to perform these checks acceptably when relatively large liquid volumes are aspirated (e.g., 30 μL or greater). However, if the volume of the aspirated sample is relatively small, the noise in the pressure signal becomes so large that it may obscure the information contained in the pressure reading. Accordingly, when the aspirated liquid volume is relatively small, it may become very difficult to robustly determine the difference between an air aspiration, i.e., where no liquid (e.g., biological liquid sample or liquid reagent) is aspirated, and a proper aspiration. Similarly, if a clot or other undesirable material were aspirated, it becomes challenging to determine the difference between the aspiration of such clot or other undesirable material and proper liquid sample aspiration at such small volume aspiration. Accordingly, there is a need for a method and apparatus to accurately determine aspiration pressure when the aspirated volume of the liquid is relatively small so that an adequate check may be carried out.

SUMMARY

In a first aspect, a method of detecting aspiration pressure during aspiration of a liquid is provided. The method includes attempting to aspirate a volume of a liquid into a probe at an aspiration rate that generates an aspiration signal having an aspiration frequency, measuring an aspiration pressure associated with the attempted aspiration of the liquid and providing a measured pressure signal, and filtering the measured pressure signal with a filter having a passband containing the aspiration frequency and attenuating frequencies of a disturbance causing noise in the measured pressure signal to obtain a filtered pressure signal.

According to another aspect, a method of detecting aspiration pressure during aspiration of a liquid is provided. The method includes attempting to aspirate a volume of a biological liquid or a liquid reagent into a probe wherein the attempted aspiration is carried out at an aspiration frequency over an aspiration cycle and the total aspirated volume is less than 25 μL, measuring with a sensor an aspiration pressure associated with the attempted aspiration and providing a measured pressure signal over at least a portion of the aspiration cycle, filtering the measured pressure signal with a filter having a passband that includes the aspiration frequency and excludes a dominant resonant frequency of a disturbance causing noise in the measured pressure signal to provide a filtered pressure signal, and verifying at an evaluation point of the filtered pressure signal whether the attempted aspiration resulted in a desired volume of biological liquid or a liquid reagent being aspirated.

According to another aspect, an aspiration apparatus is provided. The aspiration apparatus includes a probe adapted to aspirate a liquid, a pump adapted to cause the liquid to aspirate into the probe at an aspiration frequency, a pressure sensor adapted to measure an aspiration pressure during the aspiration and provide a measured pressure signal, and a filter adapted to filter the measured pressure signal, the filter having a passband containing the aspiration frequency and excluding any frequency of a disturbance causing noise in the measured pressure signal.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

BRIEF DESCRIPTION OF THE DRAWINGS

The invention will be better understood by referring to the detailed description taken in conjunction with the following drawings.

DESCRIPTION

In view of the foregoing difficulties, there is an unmet need to accurately determine aspiration quality (e.g., aspiration completeness or incompleteness) when aspirating relatively-low liquid volumes (e.g., less than about 25 µL). The apparatus and method described herein have utility for use in clinical analyzers for carrying out analyte measurements, assays, immunoassays, or other tests where liquids are aspirated and/or dispensed at low volumes. The liquids may be a liquid reagent or a biological liquid, for example. In one aspect, embodiments of the invention provide a method and apparatus that substantially reduces the signal noise present in the measured pressure signal, and, thus provides an improved ability to determine the aspiration quality during low-volume aspiration. Accordingly, using embodiments of the present invention may accurately determine aspiration pressure generated by the movement of liquid into the apparatus so that a presence of air may be readily determined and discriminated. A presence of a clog, other obstruction, or foreign material in the probe may also be determined. To address this need, embodiments of the present invention provide improved methods and apparatus to measure, process, and detect aspiration pressure. In another aspect, methods and apparatus to measure, process, and detect dispensing pressure may also be provided. Although the present invention enables low-volume discrimination, it also may be used at higher volume aspiration as well, and may improve volume aspiration discrimination and confidence even at such higher volumes (e.g., above 30 µL).

In particular, the inventor herein has discovered that in an aspiration apparatus including an aspiration pump, a probe, and a tubing (e.g., flexible tubing) coupling the probe to the pump, where a backing for accomplishing the aspiration is a liquid (e.g., purified water), fluid resonances, pump resonances, and other low-frequency resonant noises may dominate the measured pressure signal and may therefore substantially obscure the measured pressure signal with signal noise. To remove the unwanted signal noise, methods and apparatus according to embodiments of the invention filter at least the dominant noise frequencies from the measured pressure signal with a filter, such as a low-pass or other form of filter. In many cases, the dominant frequency appears to be a liquid resonance within the flexible tube. This filter is in addition to the sensor conditioning (including anti-aliasing filters and amplifier) that is commonplace for filtering sensor signals of the prior art. Such anti-aliasing filters have a cutoff frequency that is far too high to address the low frequency noise that was discovered in the low-volume aspiration measured pressure signal. In particular, the filter is designed to pass frequencies in the range of the aspiration frequency, but attenuate frequencies of the one or more disturbances. For example, a low-pass filter may have a cutoff frequency that is set at a frequency that is both above the aspiration frequency generated by the liquid aspiration event, and is below the frequency or frequencies of the pressure disturbances, or even below the dominant frequency of the disturbance in the pressure measurement signal in some embodiments. The dominant resonant frequency may be a liquid resonance.

Typically, such small volume aspirations are of volumes less than about 25 µL, less than about 20 µL, less than about 15 µL, or even less than about 10 µL in some embodiments. In some embodiments, the method and apparatus are effective to aspirate a biological liquid, and a total aspirated volume of the biological liquid is between about 1 µL and about 25 µL. In other embodiments, the method and apparatus are effective to aspirate a liquid reagent and the total aspirated volume of the liquid reagent is between about 5 µL and about 25 µL.

The filtering may be accomplished by any suitable type of low-pass filter, band-pass filter, or band-stop filter that has a cutoff frequency that cuts out frequencies that coincide with disturbances from mechanical resonances (e.g., 30 Hz-80 Hz), electrical resonances (e.g., 60 Hz), and dominant frequencies due to liquid resonances (e.g., at about 20 Hz-50 Hz) in the liquid-backed aspiration apparatus. Additionally, the filter has a passband that includes the frequency generated by an aspiration (i.e., the aspiration frequency that is typically 2.5 Hz to 20 Hz). Aspiration frequency is the frequency of a single aspiration. The filter may be an Infinite Impulse Response (IIR) filter such as a Butterworth filter, finite impulse response (FIR) filter, or other suitable low-pass, band-pass, or band-stop filter, such as any digital filter, having an appropriate cutoff or passband frequency. The cutoff frequency or passband frequency may be set based upon a lookup table or other methods based upon the previous knowledge of the aspiration frequency and the disturbances present at any particular selected aspiration rate, volume, and flow rate for an aspiration.

These and other aspects and features of embodiments of the invention will be described with reference to FIGS. 1-8 herein.

Figure 1:
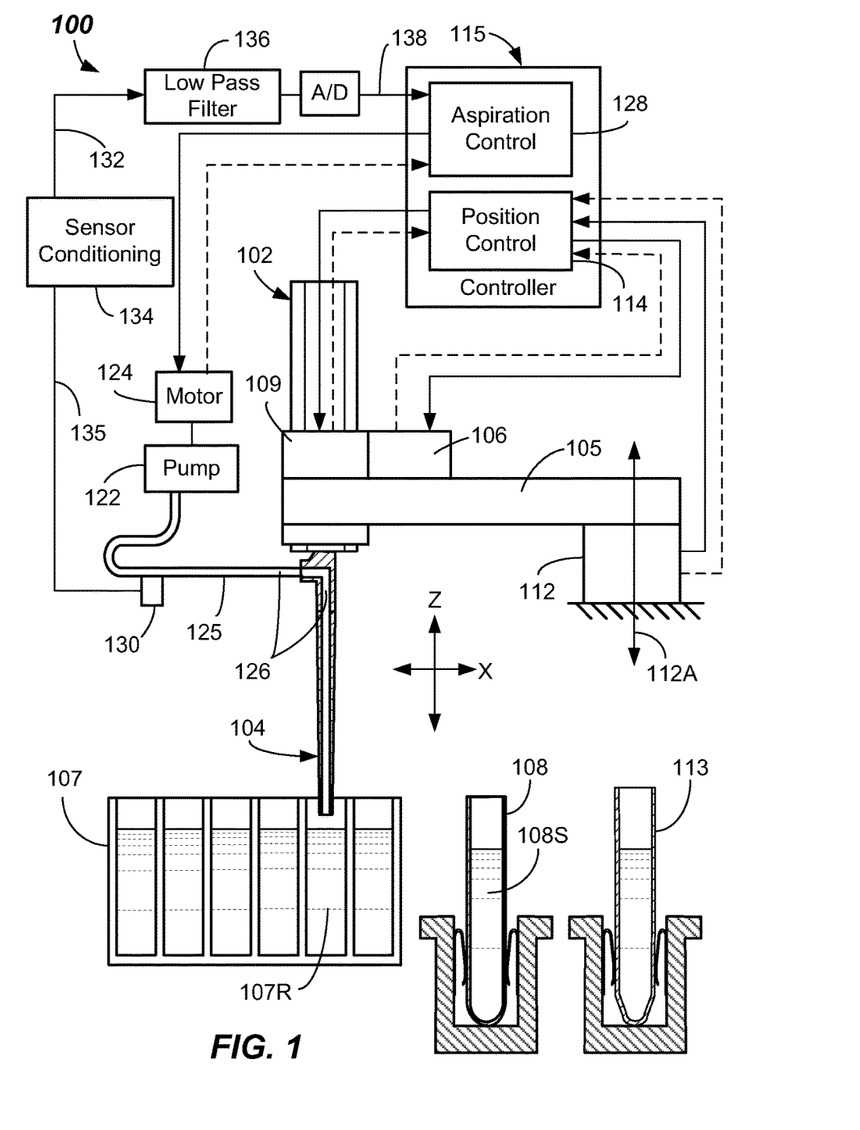
FIG. 1 illustrates a schematic diagram of an aspirating apparatus according to embodiments.

Referring to FIG. 1, a first embodiment of an aspiration apparatus 100 according to an aspect of the invention is illustrated. The aspiration apparatus 100 may include any suitable moving component 102, and a probe 104 adapted to aspirate a liquid. Liquid may also be dispensed by the aspiration apparatus 100. The moving component 102 is adapted to carry out motion of the probe 104 in one or more coordinate directions, such as X, Y (into and out of the paper), and/or Z. The moving component 102 may include a robot component 105 (e.g., robot arm, boom, frame or the like) to which the sample probe 104 may be mounted for motion. The robot component 105 may swing about a fixed axis 112A by the operation of a rotational actuator 112 to provide horizontal (e.g., Y-axis) motion capability, for example. Optionally or additionally, vertical motion of the probe 104 along a vertical Z-axis may be imparted by operation of a suitable linear actuator 109 of the moveable component 102, which may be coupled to the probe 104. The linear actuator 109 may be operable to descend and ascend the probe 104 into and out of a reagent container 107 containing a volume of a reagent liquid 107R and/or into and out of a sample container 108 containing biological liquid 108S, so that at least some may be aspirated and so that at least some may be tested. The biological liquid 108S may be blood, blood serum, plasma, cerebral liquid, spinal liquid, interstitial liquid, urine, or the like. Other liquids may be aspirated. Additionally or optionally, a linear actuator 106 may be provided to impart motion along the X-axis. Each of the actuators 106, 109, 112 may be suitably actuated under the control of a position control 114 of a controller 115 to impart the desired motions to the probe 104 in one-dimensional, two-dimensional, or three-dimensional space. Such mechanical systems that are adapted to move the probe 104 may include system and/or component mechanical resonances and may impart system noise (e.g., pressure perturbations in the backing liquid) from the operation of the actuators 106, 109, 112.

Each of the actuators 106, 109, 112 may be operated to move the probe 104 from the reagent container 107 to a reaction vessel 113 (e.g., a cuvette), and/or from the sample container 108 to the reaction vessel 113. The aspirator apparatus 100 may be provided to aspirate the desired liquid (e.g., reagent liquid 107R or biological liquid 108S) into the interior of the probe 104. The aspirated volume may be less than about 25 µL, less than about 20 µL, less than about 15 µL, or even less than about 10 µL in some embodiments. Prior systems were unable to discriminate effectively at such low volumes. In some embodiments, a dispensed volume may be less than about 25 µL, less than 20 µL, less than 15 µL, or even less than 10 µL in some embodiments.

The aspirator apparatus 100 may include a pump 122, such as a piston-type pump that may be driven by a suitable motor 124. Other types of pumps may be used. The pump 122 is adapted to cause the liquid to aspirate into the probe 104 at an aspiration rate for a predetermined period of time, which creates a pressure signal having a defined frequency (at the aspiration frequency). A range of aspiration rates achievable by the aspiration apparatus are between about 20 microliters per second and about 500 microliters per second, which creates a pressure signal frequency between about 2.5 Hz and about 30 Hz for typical volumes aspirated up to about 100 uL. The motor 124 may be a stepper motor or the like, and may also be a source of system noise causing pressure variations in the backing liquid. The pump 122 may be fluidly coupled to the probe 104 by a flexible tube 125, such as by a section of hollow Teflon tube or other suitably flexible conduit. The flexible tube 125 and the probe 104 are filled with a backing liquid 126 (e.g., purified water) to provide a suitable liquid backing to generate an appropriate vacuum pressure to allow aspiration of the various liquids (e.g., liquid reagent 107R and/or biological liquid 108S) into an inner passage of the probe 104 for transfer to the reaction vessel 113 for testing. The length of the flexible tube 125 may be between about 0.5 m and about 1.5 m. Other lengths may be used. The backing liquid within the flexible tube 125, probe 104, and chamber of the pump 122 together with the stiffness of the tube 125 and other compliances within the aspiration apparatus 100 may cause a system liquid resonance therein. This liquid resonance also contributes to signal noise, and may be a dominant contributor to the signal noise in the measured pressure signal in some embodiments.

Aspiration control 128 of the controller 115 may be adapted and operational to control the motor 124 and thus the pump 122 to draw in (e.g., aspirate) a desired amount of the liquid (e.g., reagent liquid 107R or biological liquid 108S) into the interior of the probe 104. Aspiration control 128 of the controller 115 may also control the dispensing operations performed by the aspiration apparatus 100. The aspiration apparatus 100 may include other conventional components, such as one or more valve(s), accumulator(s), distributors, or other hydraulic components (not shown) to effectuate the liquid aspiration. Any suitable apparatus for aspirating the liquid into the probe 104 may be used. For example, aspirating and dispensing systems, which may be used with the present invention, are described in U.S. Pat. Nos. 7,867,769; 7,634,378; 7,477,997; 7,186,378; 7,150,190; and 6,370,942, which are hereby incorporated by reference herein. The aspiration apparatus includes a pump 122 that may be configured to have excellent precision at low-volume aspiration and dispensing (e.g., less than 25 µL). In the depicted aspiration apparatus 100, when operated in a low-volume aspiration mode, a total aspirated volume per aspiration cycle is about 25 µL or less, or even about 20 µL or less, or even about 15 µL or less, or even about 10 µL or less in some embodiments. It should be recognized that the aspiration apparatus is capable of excellent discrimination at higher aspiration volumes, as well (e.g., greater than 30 µL). One aspiration cycle starts at the beginning of the aspiration stroke of the pump 122 and is completed at an end of the stroke of the pump 122. According to embodiments, a full cycle of an aspiration of the liquid (e.g., reagent liquid 107R or biological liquid 108S) may be completed in less than about 300 ms, or even less than about 200 ms, or even less than about 100 ms in some embodiments. In some embodiments, the aspiration cycle may be completed in between about 40 ms and about 200 ms. Other aspiration durations may be used. The aspiration frequency may be between about 2.5 Hz and about 25 Hz, for example. The aspiration flow rate may be less than about 500 µL/s, even less than about 200 µL/s, even less than about 100 µL/s, or even less than about 60 µL/s in some embodiments.

In accordance with one or more embodiments, the aspiration control 128 may also be used to verify the effectiveness of the liquid aspiration at low volumes (e.g., less than 25 µL). For example, the aspiration control 128 may determine the presence of air in the probe 104 at low volumes (e.g., less than 25 µL). In another example, the aspiration control 128 may determine the presence of a clog or other obstruction in the probe 104 at low volumes (e.g., less than 25 µL). In another aspect, an extent of the aspiration shortage (% shortage), if any, may be estimated, as will be apparent from the following.

In more detail, the aspiration pressure in the tube 125 may be measured by a suitable pressure sensor 130. The pressure sensor 130 may be a Series 26PC model pressure sensor available from Honeywell Sensing and Controls of Morristown, N.J. Other suitable pressure sensors may be used. The pressure sensor 130 is operational and adapted to provide a raw pressure signal in line 135 and a measured pressure signal in line 132 after being conditioned. The pressure sensor 130 may be located at any suitable location along the tube 125 or adjacent the pump 122 or probe 104. Sensor conditioning 134 may be provided to condition the raw pressure signal in line 135, as is conventional. This sensor conditioning 134 may include a suitable amplifier and a suitable anti-aliasing filter. The anti-aliasing filter may have a cutoff frequency of about 190 Hz or more.

Figure 2:
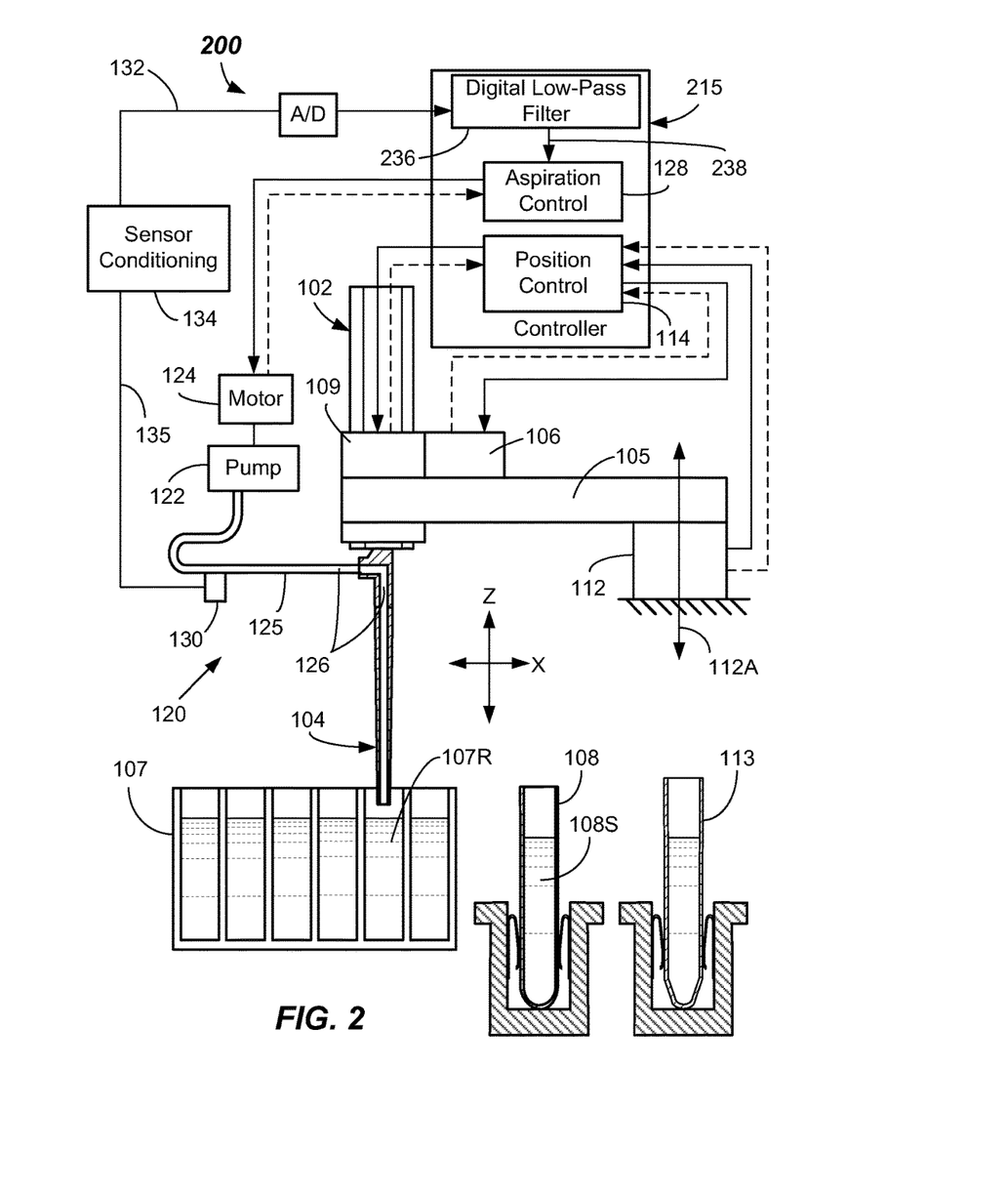
FIG. 2 illustrates a schematic diagram of an alternative aspirating apparatus according to embodiments.

According to embodiments of the invention, as shown in FIGS. 1 and 2, the aspiration apparatus 100, 200 includes a filter 136, 236 having a suitable passband. The filter 136, 236 may have a passband in the range of about 5 Hz to about 20 Hz. For example, in some embodiments where the filter 136, 236 is a low-pass filter, the low-pass filter may have a cutoff frequency of greater than about 5 Hz and less than about 20 Hz. Other cutoff frequencies may be used. In other embodiments, filter 136, 236 may be a low-pass filter and may have a cutoff frequency of greater than about 5 Hz and less than about 15 Hz. In other embodiments, the filter 136, 236 may be a low-pass filter and may have a cutoff frequency of greater than about 7 Hz and less than about 13 Hz.

The filter 136 may be a filter chip or other electrical component or circuit that accomplishes the filtering outside of the controller 115. Optionally, the filter 236 may be a digital filter wherein the filtering takes place in software within the controller 215 (see FIG. 2). In the latter case, the passband or cutoff frequency may be adjusted to account for changing aspiration conditions by the aspiration apparatus 200 that may impart different disturbance frequencies to the backing liquid 126. In the case where the filter 236 is a digital filter, the filter 236 may be a Butterworth low-pass filter. The Butterworth low-pass may have a cutoff frequency of greater than about 5 Hz and less than about 20 Hz, between about 7 Hz and about 13 Hz in some embodiments, and about 10 Hz in some embodiments. In yet other embodiments, the filter 136 may be a finite impulse response (FIR) filter. According to one or more embodiments, the order of the filter 236 may be of a higher order, or may be changed. For example, the order of the filter 236 may be a $2^{nd}$ order or above. Thus, the filter 136, 236 may be a $2^{nd}$ order filter, a $3^{rd}$ order filter, a $4^{th}$ order filter, or even of a higher-order filter. Changing an order of the filter 136 may be used to adjust an attenuation rate of the filtering of the measured pressure signal 132.

In yet other embodiments, as shown in FIG. 2, the filter 236 may be any suitable digital filter that is implemented in software by the controller 215. The controller 215 may be any suitable device including a microprocessor and memory that has the ability to generate signals to control the motor 124 and thus the pump 122 to accomplish the aspiration. The digital filter 236 of the aspiration apparatus 200 may have a passband that may be adjusted to account for situations where different aspiration frequencies, different aspiration flow rates, and/or different aspiration volumes are selected. Depending upon these apparatus variables, different passband or cutoff frequencies may be selected. For example, a lookup table stored in memory may be populated with passband settings for the digital filter 236 that are set for the filter 236 based upon at least one input such as aspiration frequency, aspiration flow rate, and/or aspiration volume. The passband or cutoff frequencies may be established based upon running experiments and determining for each variable or combination thereof, a setting for the passband or cutoff frequency. These frequency values, determined experimentally, may then be stored in a lookup table and set for any particular aspiration based upon the selected variables. In general, these same settings are used for dispensing.

In other embodiments, the measured pressure signal 132 may be subjected to a fast Fourier transform (FFT) analysis to determine the fundamental disturbance frequency of the measured signal. Once the fundamental disturbance frequency is determined, the passband for the filter 236 may be set based upon the expected frequency of the aspiration event (the aspiration frequency). For example, in some embodiments where filter 236 is a low-pass filter, the cutoff frequency of the filter 236 may be set to be greater than the aspiration frequency and lower than a frequency of the fundamental disturbance causing noise in the measured pressure signal in line 132. For example, in some embodiments, the cutoff frequency may be set between the aspiration frequency and the frequency of the fundamental disturbance as determined by the FFT analysis.

In operation, during aspiration, the robot component 105 may position the probe 104 above the container (e.g., 107 or 108) and descend the probe 104. The descent into the container (e.g., 107 or 108) is produced by the action of the linear actuator 109 under the control of the position control 114 until the probe 104 reaches a desired depth therein. The aspirator apparatus 100 may be operated via a signal from the aspiration control 128 to draw off a predefined volume of the liquid (e.g., 107R or 108S) into the inner passage of the probe 104. In accordance with a low-volume aspiration embodiment, the aspirated volume is less than about 25 μL, but aspirations larger than about 25 uL could also be performed. As the pump 122 is operated, the level of liquid (e.g., 107R or 108S) in the container (e.g., 107 or 108) is attempted to be drawn down (aspirated). When it is determined that a desired volume of liquid (e.g., 107R or 108S) has been received within the sample probe 104, as measured by aspiration control 128, the pump 122 may be stopped such that no further aspiration of the liquid (e.g., 107R or 108S) occurs. This may be determined by a suitable feedback sensor (not shown) on the motor 124 providing feedback on the position of the pump 122 or counting steps of the motor 124 when the motor 124 is a stepper motor, for example. Other suitable position feedback may be provided.

During the aspiration process, a representative raw aspiration pressure may be measured (e.g., the measured aspiration pressure) via the sensor 130. This raw measured pressure in line 135 may be conditioned by sensor conditioning 134 to provide a measured pressure signal in line 132, and then filtered by the filter 136, 236. Each embodiment may include conversion by an A/D filter. The digital filter version may be sampled as the aspiration is taking place. The sampling rate may be at any suitable rate such as 1000 samples per second. The sampling may be continuous for the entire aspiration cycle, or over any representative portion of the aspiration cycle.

Figure 3A:
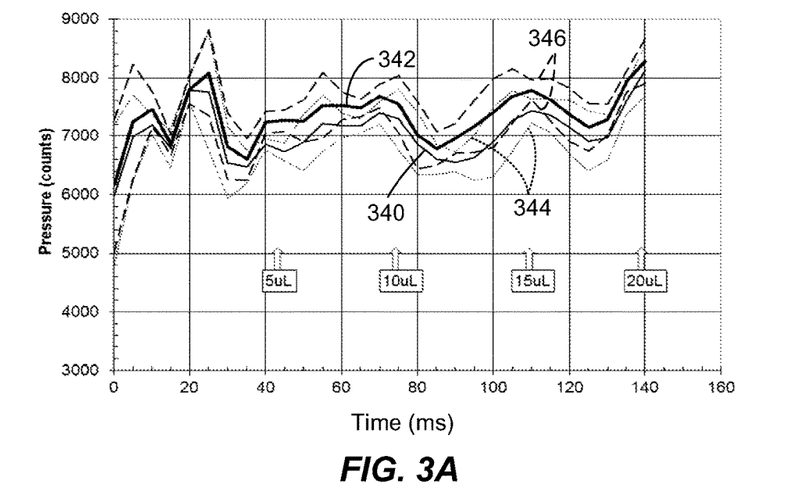
FIG. 3A illustrates a plot showing a conditioned measured pressure signal with 3 sigma error bands.

FIG. 3A illustrates an example of an aspiration taken at relatively low volume (e.g., 20 μL or less). The solid bold line 340 is a liquid aspiration, whereas the dotted bold line 342 is an air aspiration. Both are separately obtained and represent raw unfiltered, but conditioned measured pressure signals, in line 132. As can be seen, the three sigma confidence intervals 344, 346 about each signal trace 340, 342, respectively, overlap significantly to the extent that it is difficult, if not impossible, to accurately determine if the aspiration at such low volumes is of a liquid or of air. Accordingly, in prior systems, simply, there was not acceptable means based upon pressure for verifying the quality of the aspiration at such low volumes.

Figure 3B:
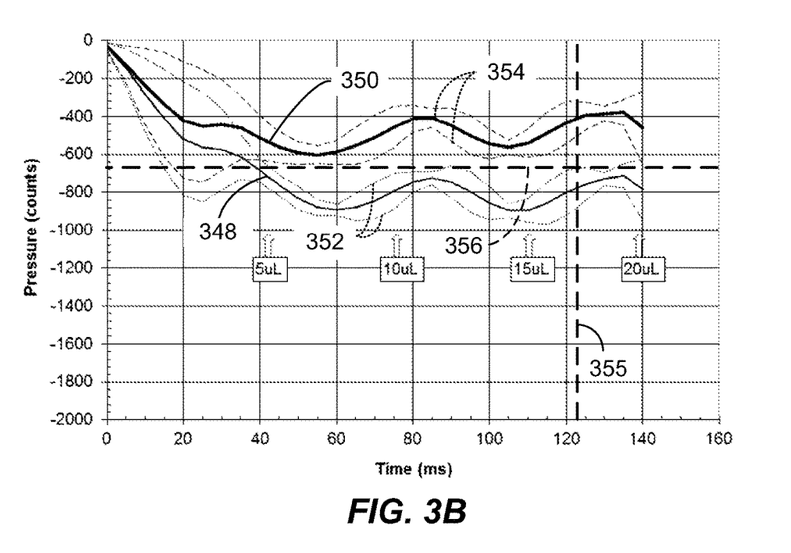
FIG. 3B illustrates a plot showing a low-pass filtered pressure signal with 3 sigma error bands according to embodiments.

FIG. 3B illustrates a low-pass filtered signal according to an aspect of embodiments of the invention with an appropriately selected passband. As can be seen, the low-pass filtered pressure signals for a liquid aspiration 348 and air aspiration 350 are significantly separated from one another. Accordingly, the three sigma confidence intervals 352, 354 about each signal trace 348, 350, respectively, no longer overlap significantly during substantial portions of the aspiration, albeit they still overlap somewhat at relatively low volumes (e.g., less than about 5 μL) in the depicted embodiment.

Thus, it is now possible using embodiments of the invention to accurately determine the aspiration quality at such low volumes of a liquid or of air. In order to verify the effectiveness (e.g., quality) of the aspiration, the filtered pressure signal 138, 238 (FIG. 1 and FIG. 2, respectively) is measured and compared at an evaluation point 355. At the desired evaluation point 355, the filtered pressure signal is compared to a pre-established threshold value 356. If the filtered pressure signal is above (has a higher absolute value) the pre-established threshold value (below the threshold line 356 shown), then the aspiration may be deemed to be successful. If the filtered pressure signal has an absolute value that is below the pre-established threshold value (above the threshold line 356 shown), then the aspiration may be deemed to be unsuccessful or incomplete. This may signify that some air was aspirated.

Similarly, because the pressure now may be discriminated at such relatively low volumes, the existence of a clot or other undesirable solid or semi-solid material in the probe 104 may be determined. Any suitable method known in the art may be used to determine if undesirable material is present.

Once it is determined that the aspiration was unsuccessful, remedial measures may include stopping, aspirating from another well in the case of insufficient reagent volume 107R, and/or obtaining additional biological liquid 108S. Optionally, the extent of aspiration shortage may be determined, and if there is an oversupply of the liquid (e.g., liquid reagent), and if the shortage is small enough, then the transfer may be completed. Further, to the extent that a smaller amount of a biological liquid 108S may be aspirated, but where the amount is known, a corresponding smaller amount of reagent liquid 107R may be aspirated for mixing therewith in the reaction vessel 113.

Figure 4A:
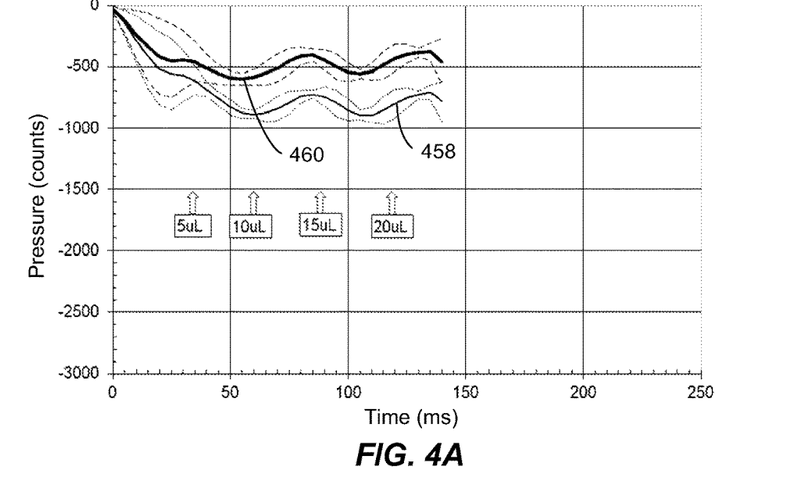
FIG. 4A illustrates a plot showing a low-pass filtered pressure signal using a $2^{nd}$ order filter according to embodiments.
Figure 4B:
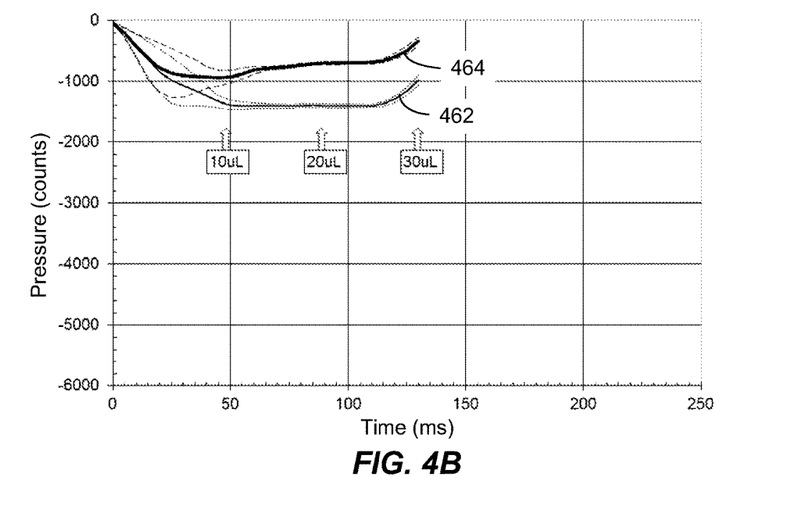
FIG. 4B illustrates a plot showing a low-pass filtered pressure signal using a higher flow rate according to embodiments.

Referring now to FIGS. 4A and 4B, several examples are provided illustrating an effect of changing the aspiration rate. In the first embodiment, 25 µL of a liquid and air has been aspirated and filtered pressure signals 458, 460 are provided. The frequency of the aspiration event (aspiration frequency) is 7.14 Hz having been aspirated over 140 ms by the aspiration apparatus 100. The aspiration rate was 150 µL/sec. A second order Butterworth filter having a 10 Hz cutoff frequency was used with a −7800 scalar count offset to center the data at zero. Good separation between the liquid aspiration signal 458 and the air aspiration signal 460 is noted for low-volume aspirations between at least 10 µL and 25 µL.

FIG. 4B illustrates an example where 30 µL of a liquid and air has been aspirated and filtered pressure signals 462, 464 are provided. The aspiration frequency is 7.14 Hz having been aspirated over about 140 ms by the aspiration apparatus 100. The aspiration rate was increased to 250 µL/sec. A 10 Hz second order Butterworth filter was used with a −7800 scalar count offset to center the data at zero. Good separation between the liquid aspiration signal 462 and the air aspiration signal 464 is noted for low-volume aspirations between at least 10 µL and 30 µL. By aspirating at a slightly higher rate in combination with the low-pass filtering, a more linear measurement region may be achieved.

Figure 5:
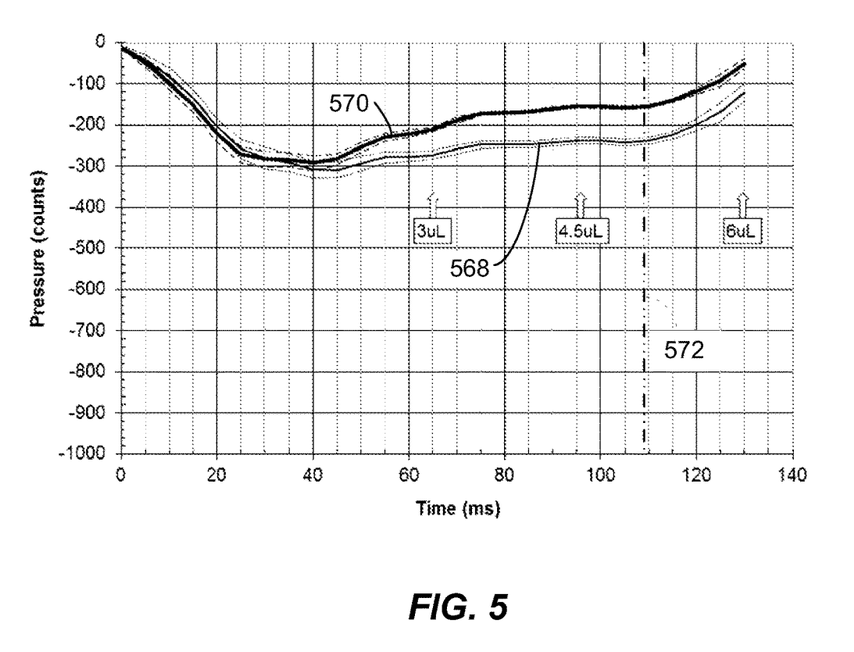
FIG. 5 illustrates a plot showing a filtered pressure signal at less than 10 µL aspiration volume according to embodiments.

FIG. 5 illustrates an example where 6 µL of a liquid and air has been aspirated and filtered pressure signals 568, 570 are provided. The frequency of the aspiration event (aspiration frequency) is about 7.7 Hz having been aspirated over 130 ms by the aspiration apparatus 100. The aspiration rate was relatively slow at 50 µL/sec. A 10 Hz second order Butterworth filter was used with a −7800 scalar count offset to center the data at zero. Good separation between the liquid aspiration signal 568 and the air aspiration signal 570 is noted for low-volume aspirations between about 3 µL and 6 µL. The evaluation point 572 may be set to coincide with the last portion of the motor 124 prior to its deceleration, which is generally very near the end of the excursion of the pump 122.

Figure 6:
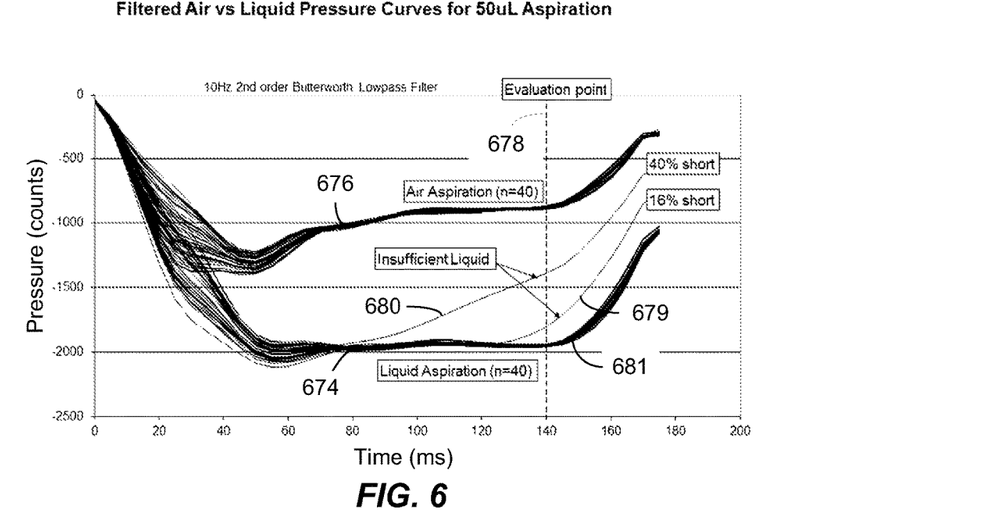
FIG. 6 illustrates a plot showing how the filtered pressure signal may be used to determine an insufficient aspiration volume according to embodiments.

FIG. 6 illustrates an example where 50 µL of a liquid and air has been aspirated and filtered pressure signals 674, 676 for liquid and air, respectively, are provided. The aspiration frequency is about 5.5 Hz having been aspirated over 180 ms by the aspiration apparatus 100. A 10 Hz second order Butterworth filter was used with a −7800 scalar count offset to center the data at zero. Good separation between the liquid aspiration signal 674 and the air aspiration signal 676 (based on 40 samples shown) is noted for volume aspirations between about 20 µL and about 40 µL. The evaluation point 678 may be set to coincide with the last stroke portion of the motor 124 prior to its deceleration, which is generally very near the end of the excursion of the pump 122. Two aspirations are shown that include insufficient liquid in the container (e.g., 107 or 108), labeled 679 (16% short) and 680 (40% short). Any suitable means for measurement of the liquid transferred between the liquid container (e.g., 107 or 108) and the reaction vessel 113 may be used to quantitatively determine the volume of liquid that was missing (the shortage) from liquid transfers 679 and 680 as 16% and 40%, respectively. From the vertical position of the crossing of the pressure trace at the evaluation point 678, a value for the percentage shortage (% short) may be obtained. The % short may be estimated by dividing the filtered pressure count value at the evaluation point 678 by an average value of baseline liquid aspiration at 681 by performing a number (e.g., 10+ runs) where it is known that a full aspiration has taken place.

Figure 7:
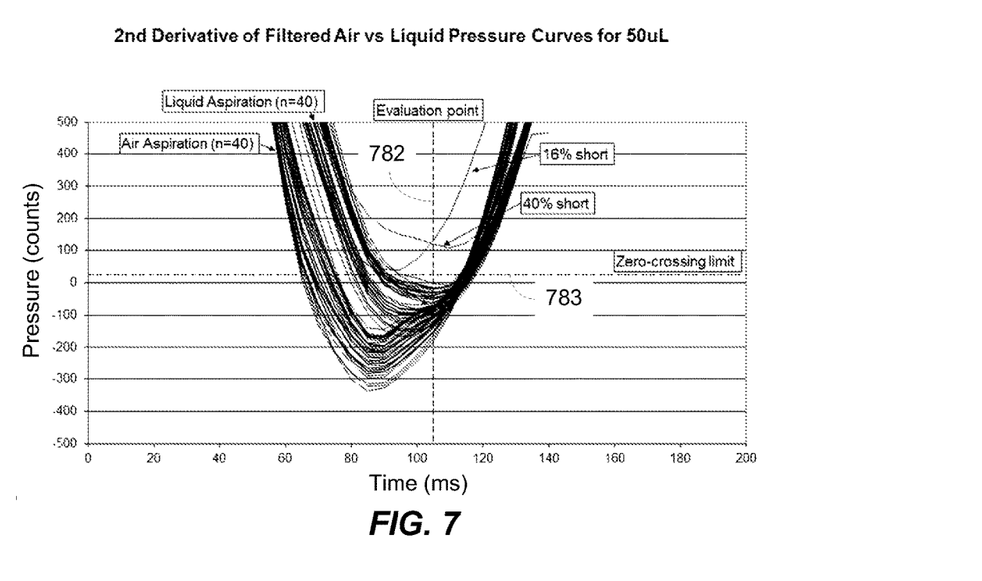
FIG. 7 illustrates a plot showing a $2^{nd}$ derivative of the filtered pressure signal according to embodiments.

FIG. 7 illustrates an example where the filtered pressure signals 674, 676 above are further processed by obtaining (e.g. taking) a second derivative thereof. The second derivative of the filtered signal may be provided by using a central difference equation (based on a Taylor series expansion). Taking the second derivative offers another means for determining whether the aspiration is complete. In particular, the second derivative at a preselected evaluation point 782 may be above a zero crossing limit 783 of the second derivative for an incomplete aspiration, i.e., will lie above the zero crossing limit 783 at the evaluation point 782. The zero crossing limit 783 may be set by conducting experiments, for example.

Other alternative post processing may be carried out on the filtered pressure signal. For example, in some embodiments, a first derivative of the filtered pressure signal may be obtained. A Taylor series expansion may be used to obtain the first derivative. In other embodiments, an integral of the filtered pressure signal may be obtained. The integral may be provided by summing individual filtered pressure values over a predetermined range around the evaluation point. In a further embodiment, a measurement of a total deviation of individual filtered pressure signal measurements at an evaluation region of the filtered pressure signal may be obtained. The total deviation of individual filtered pressure signal measurements may be compared to the filtered value at an evaluation point.

Figure 8:
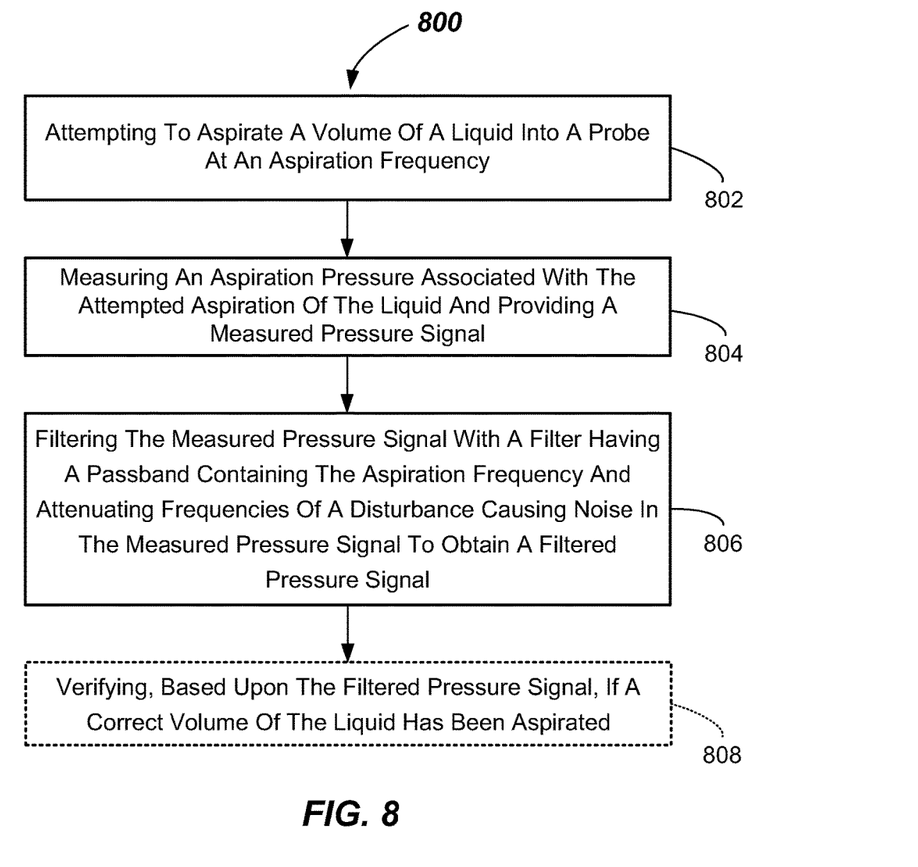
FIG. 8 is a flowchart illustrating methods according to embodiments.

Referring now to FIG. 8, a broad method of the invention is illustrated. The method 800 includes, in 802, attempting to aspirate a volume of a liquid (e.g., a biological liquid or a reagent liquid) into a probe (e.g., probe 104) at an aspiration frequency. The aspiration rate combined with the volume aspirated produces a pressure signal of the aspiration frequency. The method 800 includes measuring an aspiration pressure associated with the attempted aspiration of the liquid and providing a measured pressure signal in 804, and filtering the measured pressure signal with a filter (e.g., filter 136, 236) in 806, the filter having a passband frequency range that includes the aspiration frequency and excludes frequencies of a disturbance causing noise in the measured pressure signal. The dominant resonant frequency may be a liquid resonance in some embodiments. The cutoff frequency between the passband and the stopband may be set based upon determining the frequency of the aspiration event (the aspiration frequency) and a dominant resonant frequency, and is set between them. Based upon the filtered pressure signal, it may be verified if a correct amount of the liquid was actually aspirated in an aspiration cycle. For example, in 808, verifying, based upon the filtered pressure signal, if a correct volume of the liquid has been aspirated may be carried out. The verification may be carried out using an appropriate algorithm in order to compare the aspirated volume to a predetermined pressure threshold or pressure threshold range values. If a volume shortage occurs, this may be flagged. An estimate of the percent shortage may be provided as well, as explained above. The method is particularly effective when aspirating at relatively-low volumes, such as when the total aspirated volume per aspiration cycle is 25 µL or less.

The quality of the aspiration may be determined by comparing the filtered pressure signal magnitude to a predetermined filtered pressure signal threshold value (e.g., 356, FIG. 3B) at an evaluation point (e.g., 355, FIG. 3B). The comparison of the filtered pressure signal magnitude to the predetermined filtered pressure signal threshold value may be achieved at a portion of the aspiration cycle where greater than 50% of a total volume to be aspirated in the aspiration cycle should have been aspirated (in a full aspiration), or even where nearly all (greater than 90%) of a total volume to be aspirated in the aspiration cycle should have been aspirated (in a full aspiration). In some embodiments, the predetermined filtered pressure signal threshold value may be based upon a percentage of an air aspiration baseline.

The above-described techniques may also be applied when the previously aspirated liquid is dispensed into a vessel to determine if the desired amount of material was dispensed.

Having shown the preferred embodiments, those skilled in the art will realize many variations are possible that will still be within the scope of the claimed invention. Therefore, it is the intention to limit the invention only as indicated by the scope of the claims.

What is claimed is:

1. A method of detecting aspiration pressure during aspiration of a liquid, comprising:
    attempting to aspirate a volume of a liquid into a probe at an aspiration frequency over an aspiration cycle, wherein the total aspirated volume per aspiration cycle is 25 µL or less;
    measuring an aspiration pressure associated with the attempted aspiration of the liquid and providing a measured pressure signal; and
    filtering the measured pressure signal with a filter having a passband containing the aspiration frequency and attenuating frequencies of a disturbance causing noise in the measured pressure signal to obtain a filtered pressure signal.

2. The method of claim 1, wherein the filter comprises a passband containing frequencies in the range of about 1 Hz to about 20 Hz.

3. The method of claim 1, wherein the filter is a low-pass filter comprising a cutoff frequency of greater than about 3 Hz and less than about 20 Hz.

4. The method of claim 1, wherein the filter is a low-pass filter comprising a Butterworth low-pass filter.

5. The method of claim 1, wherein the filter is a low-pass filter comprising an infinite impulse response filter.

6. The method of claim 1, wherein the filter is a low-pass filter comprising a finite impulse response filter.

7. The method of claim 1, wherein the filter comprises a digital filter.

8. The method of claim 1, further comprising setting the passband frequency based upon determining the aspiration frequency and a dominant resonant frequency.

9. The method of claim 1, wherein the total aspirated volume per aspiration cycle is 10 µL or less.

10. The method of claim 1, further comprising changing an order of the low-pass filter to adjust an attenuation rate of the filtering.

11. The method of claim 1, further comprising providing an order of the low-pass filter to be second order or above.

12. The method of claim 1, further comprising measuring the disturbance frequencies and setting the passband and attenuation rate of the filter to exclude the disturbance frequencies.

13. The method of claim 1, further comprising:
    determining a presence of aspirated air based upon the filtered pressure signal.

14. The method of claim 1, further comprising:
    determining a presence of a clog or other undesirable material based upon the filtered pressure signal.

15. The method of claim 1, further comprising:
    obtaining a second derivative of the filtered pressure signal.

16. The method of claim 1, further comprising:
    obtaining a first derivative of the filtered pressure signal.

17. The method of claim 1, further comprising:
    obtaining an integral of the filtered pressure signal.

18. The method of claim 1, further comprising:
    obtaining a measurement of a total deviation of individual filtered pressure signal measurements at an evaluation region of the filtered pressure signal.

19. The method of claim 1, further comprising:
    determining, based upon the filtered pressure signal, a percent shortage of the aspiration.

20. The method of claim 1, wherein the liquid comprises a liquid biological sample or a liquid reagent.

21. The method of claim 1, wherein the liquid comprises a liquid biological sample and a total aspirated volume of the liquid biological sample is between about 1 µL and about 25 µL per aspiration cycle.

22. The method of claim 1, wherein the liquid comprises a liquid reagent and the total aspirated volume of the liquid reagent is between about 5 µL and about 25 µL per aspiration cycle.

23. The method of claim 1, further comprising verifying, based upon the filtered pressure signal, if a correct amount of the liquid was actually aspirated in an aspiration cycle.

24. The method of claim 23, wherein the comparing the filtered pressure signal magnitude to the predetermined filtered pressure signal threshold value is achieved at a portion of the aspiration cycle where greater than 50% of a total volume to be aspirated in the aspiration cycle should have been aspirated.

25. The method of claim 23, further comprising basing the predetermined filtered pressure signal threshold value upon a percentage of an air aspiration baseline.

26. The method of claim 23, wherein the determining comprises comparing a filtered pressure signal magnitude to a predetermined filtered pressure signal threshold value at an evaluation point.

27. The method of claim 26, wherein the comparing the filtered pressure signal magnitude to the predetermined filtered pressure signal threshold value is achieved at a portion of the aspiration cycle where greater than 50% of a total volume to be aspirated in the aspiration cycle should have been aspirated.

28. A method of detecting aspiration pressure during aspiration of a liquid, comprising:

attempting to aspirate a volume of a biological liquid or a liquid reagent into a probe wherein the attempted aspiration is carried out at an aspiration frequency over an aspiration cycle and the total aspirated volume is less than 25 µL per aspiration cycle;

measuring with a sensor an aspiration pressure associated with the attempted aspiration and providing a measured pressure signal over at least a portion of the aspiration cycle;

filtering the measured pressure signal with a filter having a passband that includes the aspiration frequency and excludes a dominant resonant frequency of a disturbance causing noise in the measured pressure signal to provide a filtered pressure signal; and verifying at an evaluation point of the filtered pressure signal whether the attempted aspiration resulted in a desired volume of biological liquid or a liquid reagent being aspirated.

29. An aspiration apparatus, comprising:

a probe adapted to aspirate a liquid;

a pump adapted to cause the liquid to aspirate into the probe at an aspiration frequency over an aspiration cycle, wherein the total aspirated volume per aspiration cycle is 25 µL or less;

a pressure sensor adapted to measure an aspiration pressure during the aspiration and provide a measured pressure signal; and a filter adapted to filter the measured pressure signal, the filter having a passband containing the aspiration frequency and excluding any frequency of a disturbance causing noise in the measured pressure signal.

30. The aspiration apparatus of claim 29, further comprising a tube including a backing liquid coupled to the probe.

31. The aspiration apparatus of claim 29, wherein the pump is adapted to cause the liquid to dispense from the probe.

\* \* \* \* \*